(12) United States Patent
Chassot et al.

(10) Patent No.: US 6,600,050 B2
(45) Date of Patent: Jul. 29, 2003

(54) DIAMINOPYRAZOLE DERIVATIVES AND DYES CONTAINING SAID COMPOUNDS

(75) Inventors: Laurent Chassot, Praroman (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 10/221,295

(22) PCT Filed: Oct. 18, 2001

(86) PCT No.: PCT/EP01/12061

§ 371 (c)(1),
(2), (4) Date: Sep. 9, 2002

(87) PCT Pub. No.: WO02/072556

PCT Pub. Date: Sep. 19, 2002

(65) Prior Publication Data

US 2003/0115684 A1 Jun. 26, 2003

(30) Foreign Application Priority Data

Mar. 13, 2001 (DE) .......................................... 101 11 862

(51) Int. Cl.$^7$ ............................................. C07D 487/02
(52) U.S. Cl. ................................ 548/364.4; 548/371.7; 8/409
(58) Field of Search ........................... 548/371.7, 364.4; 8/409

(56) References Cited

U.S. PATENT DOCUMENTS 6,099,592 A    8/2000    Vidal et al.

FOREIGN PATENT DOCUMENTS

| DE | 42 34 886 A1 | 4/1994 |
| DE | 201 10 357 U | 9/2001 |
| EP | 0 740 931 A1 | 11/1996 |
| EP | 0 786 244 A | 7/1997 |

*Primary Examiner*—Robert W. Ramsuer
(74) *Attorney, Agent, or Firm*—Michael J. Striker

(57) ABSTRACT

Diaminopyrazole derivatives of the general Formula (I) or their physiological tolerated, water-soluble salts with inorganic or organic acids,

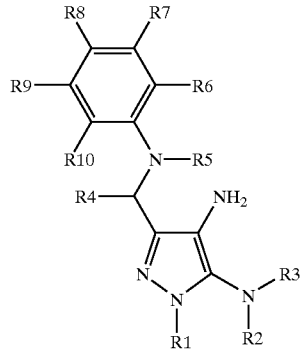

(I)

and agents, containing these compounds, for the oxidative dyeing of fibers.

12 Claims, No Drawings

DIAMINOPYRAZOLE DERIVATIVES AND DYES CONTAINING SAID COMPOUNDS

The invention relates to new diaminopyrazole derivatives, as well as to agents containing these compounds for dyeing keratin fibers.

In the field of dyeing keratin fibers, especially of dyeing hair, oxidation dyes have achieved appreciable importance. The dyeing takes place here by the reaction of certain developer substances with certain coupler substances in the presence of suitable oxidizing agents. As developer substances, especially 2,5-diaminotoluene, 2,5-diaminophenylethyl alcohol, p-aminophenol and 4,5-diaminopyrazole derivatives are used and, as coupler substances, resorcinol, 4-chlororesorcinol, 1-napthol, 3-aminophenol and derivates of m-phenylenediamine may be mentioned.

Oxidation dyes, which are used to dye human hair, must satisfy numerous requirements in addition to dyeing the hair in the desired intensity. For example, the dyes must be safe from a toxicological and dermatological point of view and the hair dyeings achieved must have good light fastness, acid fastness and crocking fastness and not interfere with permanent wave stability. In any case, however, such dyeings, in the absence of the effects of light, rubbing, and chemical agents, must remain stable for a period of at least 4 to 6 weeks. In addition, it is necessary that a broad palette of different color nuances can be produced by combinations of suitable developer substances and coupler substances. Until now, to cover the increasingly important red region, primarily 4-aminophenol was widely used as a developer. The use of certain diaminopyrazole derivatives in oxidation hair dyeing agents is known from the EP-OS 740 931, DE-OS-42 34 886 and EP-OS 0 786 244. However, the requirements, which must be met by oxidation dyes, are not fulfilled in every respect by these compounds. For example, the dyeings obtained in some cases do not have a satisfactory color intensity and/or pure red shades are not obtained. There is therefore a continued need for new developer substances which fulfill the aforementioned requirements particularly well.

For this purpose, it has now surprisingly been found that new diaminopyrazole derivates of the general Formula (I) fulfill the requirements imposed on developer substances particularly well. For example, color nuances, which are exceedingly intensive, light fast and wash fast, are obtained using these developer substances with most of the known coupler substances.

The object of the present invention therefore are diaminopyrazole derivatives of the general formula (I) or their physiologically tolerated, water soluble salts with inorganic or organic acids

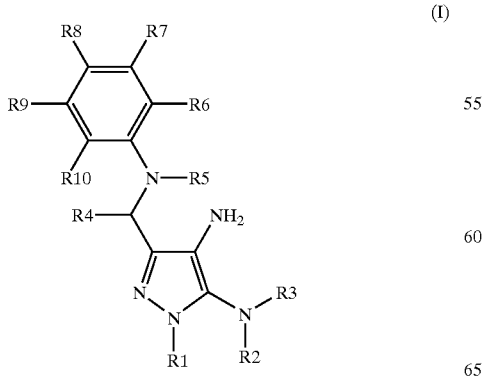

wherein

R1 represents a $C_1$–$C_6$ alkyl group, a $C_2$–$C_4$ hydroxyalkyl group, a $C_3$–$C_4$ dihydroxyalkyl group or a $C_2$–$C_6$ alkoxy ($C_1$–$C_2$) alkyl group, a phenyl group, a benzyl group or a substituted benzyl group;

R2 and R3 independently of one another are hydrogen, a $C_1$–$C_6$ alkyl group, a hydroxy ($C_2$–$C_4$) alkyl group, a dihydroxy ($C_3$–$C_4$) alkyl group or a $C_2$–$C_4$ alkoxy ($C_1$–$C_2$) alkyl group or R2 and R3, together with the nitrogen, form a 4-member to 8-member heteroaliphatic ring;

R4 represents hydrogen or a $C_1$–$C_6$ alkyl group;

R5 is hydrogen, a $C_1$–$C_6$ alkyl group, an unsaturated $C_2$–$C_6$ alkyl group, a hydroxy ($C_2$–$C_4$) alkyl group, a dihydroxy ($C_3$–$C_4$) alkyl group, an amino ($C_2$–$C_4$) alkyl group, a dimethylamino ($C_2$–$C_4$) alkyl group, an acetylamino ($C_2$–$C_4$) alkyl group, a methoxy ($C_2$–$C_4$) alkyl group, an ethoxy ($C_2$–$C_4$) alkyl group, a $C_1$–$C_4$ cyanoalkyl group, a carboxy ($C_1$–$C_4$) alkyl group or an aminocarbonyl ($C_1$–$C_4$) alkyl group;

R6, R7, R8, R9, R10 independently of one another represent hydrogen, a halogen atom (F, Cl, Br, I), a cyano group, a hydroxy group, a $C_1$–$C_4$ alkoxy group, a hydroxy ($C_2$–$C_4$) alkoxy group, a $C_1$–$C_6$ alkyl group, a $C_1$–$C_4$ alkylthioether group, a mercapto group, a nitro group, an amino group, a ($C_1$–$C_4$) alkylamino group, a hydroxy ($C_2$–$C_4$) alkylamino group, a di($C_1$–$C_4$) alkylamino group, a di(hydroxy($C_2$–$C_4$)alkyl) amino group, a (dihydroxy($C_3$–$C_4$)alkyl) amino group, a (hydroxy ($C_2$–$C_4$)alkyl)-($C_1$–$C_4$)alkylamino group, a trifluoromethyl group, a —C(O)H group, a —C(O)$CH_3$ group, a —C(O)$CF_3$ group, an —Si$(CH_3)_3$ group, a hydroxy ($C_2$–$C_4$) alkyl group or a dihydroxy($C_3$–$C_4$) alkyl group or two adjacent R6 to R10 groups form an —O—CH2—O— bond.

As compounds of Formula (I), the following may be mentioned by way of example:

2-isopropyl-5-phenylaminomethyl-2H-pyrazole-3,4-diamine, 4-[(4,5-diamino-1-isopropyl-1H-pyrazole-3-ylmethyl)-amino]-phenol, 3-[(4,5-diamino-1-isopropyl-1H-pyrazole-3-ylmethyl)-amino]-phenol, 5-[(4,5-diamino-1-isopropyl-1H-pyrazole-3-ylmethyl)-amino]-2-methyl-phenol, 5[(3,4-dimethoxy-phenylamino)-methyl]-2-isopropyl -2H-pyrazole-3,4-diamine, 2-[(4,5-diamino-1-isopropyl-1H-pyrazole-3-ylmethyl)-amino]-4-nitro-phenol, 5-[(3-amino-phenylamino)-methyl]-2-isopropyl-2H-pyrazole-3,4-diamine, 5-[(4-amino-phenylamino)-methyl]-2-isopropyl-2H-pyrazole-3,4-diamine, 5[(4-amino-2 or 3-methyl-phenylamino)-methyl]-2-isopropyl-2H-pyrazole-3,4-diamine, 2-{5 or 6-amino-2 or 3-[(4,5-diamino-1-isopropyl-1H-pyrazole-3-ylmethyl)-amino]-phenyl}-ethanol, 2-{4-amino-2-[(4,5-diamino-1-isopropyl-1H-pyrazole-3-ylmethyl)-amino]-phenoxy}-ethanol, 5-[(4-dimethylamino-phenylamino)-methyl]-2-isopropyl-2H-pyrazole-3,4-diamine, 2-{4,5-diamino-3-[(3-amino-phenylamino)-methyl]-pyrazole-1-yl}-ethanol, 2-{4,5-diamino-3-[(4-amino-phenylamino)-methyl]-pyrazole-1-yl}-ethanol, 2-{4,5-diamino-3-[(4-amino-2-methyl-phenylamino)-methyl]-pyrazole-1-yl}-ethanol, 2-(4,5-diamino-3-{[4-amino-2-(2-hydroxy-ethyl)-phenylamino]-methyl}-pyrazole-1-yl)-ethanol, 2-{4,5-diamino-3-[(4-dimethylamino-phenylamino)-methyl]-pyrazole-1-yl}-ethanol, 2-[4,5-diamino-3-(benzo[1,3]dioxol-5-yl-aminomethyl)-pyrazole-1-yl]ethanol, 4-chloro-2-{[4,5-diamino-1-(2-hydroxy-ethyl)-1H-pyrazole-3-ylmethyl]-amino}-phenol, 2-(4,5-diamino-3-phenylaminomethyl-pyrazole-1-yl)-ethanol, 4-{[4,5- diamino-1-(2-hydroxy-ethyl)-1H-pyrazole-3-ylmethyl]-amino} phenol, 3-{[4,5-diamino-1-(2-hydroxyethyl)-1H-pyrazole-3-ylmethyl]-amino}-phenol, 5-{[4,5-diamino-1-(2-hydroxy-ethyl)-1H-pyrazole-3-ylmethyl]-amino}-2-methyl-phenol, 2-{[4,5-diamino-3-[(3,4-dimethoxy-phenylamino)-methyl]-pyrazole-1-yl}-ethanol, 2-{[4,5-diamino-1-(2-hydroxy-ethyl)-1H-pyrazole-3-ylmethyl]-amino}-4-nitro-phenol, 2-(4-methyl-benzyl)-5-phenylaminomethyl-2H-pyrazole-3,4-diamine, 2-benzyl-5-phenylaminomethyl-2H-pyrazole-3,4-diamine, 2-methyl-5-phenylaminomethyl-2H-pyrazole-3,4-diamine, 2-phenyl-5-phenylaminomethyl-2H-pyrazole-3,4-diamine, 2-t-butyl-5-phenyl-aminomethyl-2H-pyrazole-3,4-diamine, 5-[(4-amino-phenylamino)-methyl]-2-(4-methyl-benzyl)-2H-pyrazole-3,4-diamine, 5-[(4-amino-phenylamino)-methyl]-2-benzyl-2H-pyrazole-3,4-diamine, 4-[(4,5-diamino-1-(4-methyl-benzyl)-1H-pyrazole-3-ylmethyl)-amino]phenol, 4-[(4,5-diamino-1-benzyl-1H-pyrazole-3-ylmethyl)-amino]-phenol.

Preferred are compounds of Formula (I), in which (i) R2 and R3 represent hydrogen and R1 represents a $C_1$–$C_4$ alkyl group, a $C_2$–$C_4$ hydroxyalkyl group, a benzyl group or a methylbenzyl group and/or (ii) R2, R3, R4 and R5 represent hydrogen and R1 represents a $C_1$–$C_4$ alkyl group, a $C_2$–$C_4$ hydroxyalkyl group, a benzyl group or a methylbenzyl group, and/or (iii) R2, R3, R4 and R5 represent hydrogen and R1 represents a $C_1$–$C_4$ alkyl group, a $C_2$–$C_4$ hydroxyalkyl group, a benzyl group or a methylbenzyl group, and at least one of the R6 to R10 groups is a hydroxy group or an amino group, while the remaining R6 to R10 groups are hydrogen.

In particular, the following compounds or their salts with inorganic or organic acids may be mentioned:

4-{[4,5-diamino-1-(2-hydroxy-ethyl)-1H-pyrazole-3-ylmethyl]-amino}-phenol, 2-{4,5-diamino-3-[(4-amino-phenylamino)-methyl]-pyrazole-1-yl}-ethanol, 2-(4,5-diamino-3-phenylaminomethyl-pyrazole-1-yl)-ethanol, 2-isopropyl-5-phenylaminomethyl-2H-pyrazole-3,4-diamine, 2-{4,5-diamino-3-[(3-amino-phenylamino)-methyl]-pyrazole-1-yl}-ethanol, 2-{4,5-diamino-3-[(4-amino-2-methyl-phenylamino)-methyl]-pyrazole-1-yl}-ethanol, 2-{4,5-diamino-3-[(4-amino-3-methyl-phenylamino)-methyl]-pyrazole-1-yl}-ethanol, 2-(4,5-diamino-3-{[4-amino-2-(2-hydroxyethyl)-phenylamino]-methyl}-pyrazole-1-yl)-ethanol, 2-(4,5-diamino-3-{[4-amino-3-(2-hydroxyethyl)-phenylamino]-methyl}-pyrazole-1-yl)-ethanol, 2-{4,5-diamino-3-[(4-dimethylamino-phenylamino)-methyl]-pyrazole-1-yl}-ethanol, 2-[4,5-diamino-3-(benzo[1,3]dioxol-5-ylaminomethyl)-pyrazole-1-yl]-ethanol, 4-chloro-2-{[4,5-diamino-1-(2-hydroxyethyl)-1H-pyrazole-3-ylmethyl]-amino}-phenol, 3-{[4,5-diamino-1-(2-hydroxyethyl)-1H-pyrazole-3-ylmethyl]-amino}-phenol, 5-{[4,5-diamino-1-(2-hydroxyethyl)-1H-pyrazole-3-ylmethyl]-amino}-2-methyl-phenol, 2-{4,5-diamino-3-[(3,4-dimethoxy-phenylamino)-methyl]-pyrazole-1-yl}-ethanol, 2-{[4,5-diamino-1-(2-hydroxy-ethyl)-1H-pyrazole-3-ylmethyl]-amino}-4-nitro-phenol, 4-[(4,5-diamino-1-isopropyl-1H-pyrazole-3-ylmethyl)-amino]-phenol, 3-[(4,5-diamino-1-isopropyl-1H-pyrazole-3-ylmethyl)-amino]-phenol, 5-[(4,5-diamino-1-isopropyl-1H-pyrazole-3-ylmethyl)-amino]-2-methyl-phenol, 5-[(3,4-dimethoxy-phenylamino)-methyl]-2-isopropyl-2H-pyrazole-3,4-diamine, 2-[(4,5-diamino-1-isopropyl-1H-pyrazole-3-ylmethyl)-amino]-4-nitro-phenol, 5-[(3-amino-phenylamino)-methyl]-2-isopropyl-2H-pyrazole-3,4-diamine, 5-[(4-amino-phenylamino)-methyl]-2-isopropyl-2H-pyrazole-3,4-diamine, 5-[(4-amino-2-methyl-phenylamino)-methyl]-2-isopropyl-2H-pyrazole-3,4-diamine, 5-[(4-amino-3-methyl-phenylamino)-methyl]-2-isopropyl-2H-pyrazole-3,4-diamine, 2-{5-amino-2-[(4,5-diamino-1-isopropyl-1H-pyrazole-3-ylmethyl)-amino]-phenyl}-ethanol, 2-{6-amino-3-[(4,5-diamino-1-isopropyl-1H-pyrazole-3-ylmethyl)-amino]-phenyl}-ethanol, 2-{4-amino-2-[(4,5-diamino-1-isopropyl-1H-pyrazole-3-ylmethyl)-amino]-phenoxy}-ethanol and 5-[(4-dimethylamino-phenylamino)-methyl]-2-isopropyl-2H-pyrazole-3,4-diamine.

The compounds of Formula (I) may be used as free bases, as well as in the form of their physiologically tolerated salts with inorganic or organic acids, such as hydrochloric acid, sulfuric acid, phosphoric acid, acetic acid, propionic acid, lactic acid or citric acid.

The inventive diaminobenzene derivatives of Formula (I) can be synthesized using known methods. The inventive compounds can be synthesized, for example, by a reductive amination of a substituted pyrazole of Formula (II)

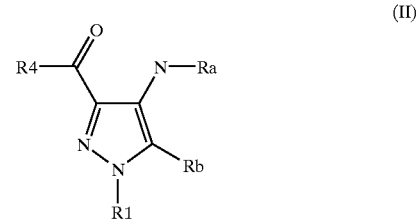

(II)

with an amine of Formula (III)

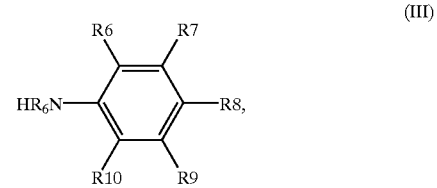

(III)

in which

Ra represents a protective group, as described, for example, in the chapter "Protective groups" in Organic Synthesis, Chapter 7, Wiley Interscience, 1991, Rb represents NR2Ra or NR2R3, and the R1 to R10 groups have the meanings given in Formula (I), the protective group subsequently being split off.

The inventive diaminopyrazole derivatives of Formula (I) are readily soluble in water and make possible dyeings with a high color intensity and excellent color fastness, especially as far as the light fastness, wash fastness and resistance to crocking are concerned. Furthermore, the compounds of Formula (I) furthermore have an excellent shelf life, particularly as components of the dyeing agents described below.

A further object of the present invention therefore are agents for the oxidative dyeing of keratin fibers, such as hair, fur, feathers or wool, especially human hair, on the basis of a combination of developer and coupler substances, which contain, as developer substance, at least one diaminopyrazole derivative of Formula (I).

The diaminopyrazole derivative of Formula (I) is contained in the inventive dyeing agent in an amount of about 0.005 to 20 percent by weight, an amount of 0.01 to 5 percent by weight and especially of 0.1 5o 2.5 percent by weight being preferred.

As coupler substances, preferably N-(3-dimethylaminophenyl)-urea, 2,6-diamino-pyridine, 2-amino-4-[(2-hydroxyethyl)-amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxy-ethyl)amino]-1,5-dimethoxybenzene, 2,3-diamino-6-methoxy-pyridine, 3-amino-6-methoxy-2-(methylamino)-pyridine, 2,6-diamino-3,5-dimethoxy-pyridine, 3,5-diamino-2,6-dimethoxy-pyridine, 1,3-diaminobenzene, 2,4-diamino-1-(2-hydroxyethoxy)-benzene, 2,4-diamino-1-(3-hydroxypropoxy)-benzene, 2,4-diamino-1-(3-methoxypropoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[(di(s-hydroxy-ethyl)amino]-aniline, 4-amino-2-di[(2-hydroxyethyl)amino]-1-ethoxybenzene, 5-methyl-2-( 1-methylethyl)-phenol, 3-[(2-hydroxyethyl)amino]-aniline, 3-[(2-aminoethyl)-amino]-aniline, 1,3-di(2,4-diaminophenoxy)-propane, di(2,4-diaminophenoxy)-methane, 1,3-diamino-2,4-dimethoxybenzene, 2,6-bis(2-hydroxyethyl)amino-toluene, 4-hydroxyindole, 3-dimethylamino-phenol, 3-diethylamino-phenol, 5-amino-2-methyl-phenol, 5-amino-4-fluoro-2-methyl-phenol, 5-amino-4-methoxy-2-methyl-phenol, 5-amino-4-ethoxy-2-methyl-phenol, 3-amino-2,4-dichloro-phenol, 3-amino-2-methyl-phenol, 3-amino-2-chloro-6-methyl-phenol, 3-amino-phenol, 2-[(3-hydroxyphenyl)-amino]-acetamide, 5-[(2-hydroxy-ethyl)amino]-2-methyl-phenol, 3-[(2-hydroxy-ethyl)amino]-phenol, 3-[(2-methoxyethyl)amino]-phenol, 5-amino-2-ethyl-phenol, 2-(4-amino-2-hydroxyphenoxy)-ethanol, 5-[(3-hydroxypropyl)amino]-2-methyl-phenol, 3-[(2,3-dihydroxypropyl)-amino]-2-methyl-phenol, 3-[(2-hydroxyethyl)-amino]-2-methyl-phenol, 2-amino-3-hydroxy-pyridine, 5-amino-4-chloro-2-methyl-phenol, 1-naphthol, 1,5-dihydroxy-naphthalene, 1,7-dihydroxy-naphthalene, 2,3-dihydroxy-naphthalene, 2,7-dihydroxy-naphthalene, 2-methyl-1-naphthol-acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 1,3-dihydroxy-2,4-dimethylbenzene, 3,4-methylenedioxy-phenol, 3,4-methylenedioxy-aniline, 5-[(2-hydroxyethyl)amino]-1,3-benzodioxol, 6-bromo-1-hydroxy-3,4-methylenedioxy-benzene, 3,4-diamino-benzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxy-indole, 5,6-dihydroxy-indoline, 4-hydroxy-indole, 5-hydroxy-indole, 6-hydroxy-indole, 7-hydroxy-indole and 2,3-indolindione, or their salts come into consideration.

Although the advantageous properties of the diaminopyrazole derivatives of the general Formula (I), which are described here, suggest that these be used as the only developer substance, it is, of course, also possible to use the diaminopyrazole derivatives of the general Formula (I) together with known developer substances, such as 1,4-diaminobenzene (p-phenylenediamine), 1,4-diamino-2-methylbenzene (p-toluylenediamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylamino-aniline, 4-dimethylamino-aniline, 4-diethylamino-aniline, 4-[di(2-hydroxyethyl)amino]-aniline, 4-[(2-methoxyethyl)amino]-aniline, 4-[(3-hydroxypropyl)amino]-aniline, 1,4-diamino-2-(2-hydroxyethyl)-benzene, 1,4-diamino-2-(1-hydroxyethyl)-benzene, 1,4-diamino-2-(1-methylethyl)-benzene, 1,3-bis[(4-aminophenyl)-(2-hydroxyethyl)amino]-2-propanol, 1,8-bis(2,5-diaminophenoxy)-3,6-dioxaoctane, 4-amino-phenol, 4-amino-3-methyl-phenol, 4-methylamino-phenol, 4-amino-2-(aminomethyl)-phenol, 4-amino-2-[(2-hydroxyethyl)-amino]methyl-phenol, 4-amino-2-(methoxymethyl)-phenol, 4-amino-2-(2-hydroxyethyl)-phenol, 5-amino-salicylic acid, 2,5-diamino-pyridine, 2,4,5,6-tetraamino-pyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-phenyl-1H-pyrazole, 4,5-diamino-1-(2-hydroxyethyl)-3-methyl-1H-pyrazole, 2-amino-phenol, 2-amino-6-methyl-phenol and 2-amino-5-methyl-phenol or their salts.

The coupler and developer substances may be contained in the inventive dyeing agents by themselves or in admixture with one another, the total amount of coupler substances and of developer substances in the inventive dyeing agent (based on the total amount of the dyeing agent) in each case being 0.005 to 20 percent by weight, preferably about 0.01 to 5 percent by weight and particularly 0.1 to 2.5 percent by weight.

The total amount of the combination of the developer and coupler substances, contained in the dyeing agent described here, preferably is about 0.01 to 20 percent by weight, an amount of about 0.02 to 10 percent by weight and, in particular, 0.2 to 6 percent by weight being particularly preferred. The developer substances and coupler substances are generally used in about equimolar amounts; however, it is not, however, disadvantageous if the developer substances or the coupler substances are present in this regard in a certain excess.

Moreover, the inventive dyeing agent may additionally contain other dye components, such as 6-amino-2-methylphenol and 2-amino-5-methylphenol.

The compounds of Formula (I) can of course also be used in combination with conventional substantive anionic, cationic, zwitterionic or nonionic dyes. The preferred anionic dyes include, for example, 6-hydroxy-5-[(4-sulfophenyl)azo]-2-naphthalene disodium sulfonate (CI15985; Food Yellow No. 3; FD&C Yellow No. 6), 2,4-dinitro-1-naphthol-7-disodium sulfonate (CI10316; Acid Yellow No. 1; Food Yellow No. 1), 2-(indane-1,3-dione-2-yl)quinoline-x,x-sulfonate (mixture of mono and disulfonate) (CI47005; D&C Yellow No. 10; Food Yellow No. 13, Acid Yellow No. 3), 5-hydroxy-1-(4-sulfophenyl)-4-[(4-sulfophenyl)azo]-pyrazole-3-trisodium carbonate (CI19140; Food Yellow No. 4; Acid Yellow No. 23), 9-(2-carboxyphenyl)-6-hydroxy-3H-xanthene-3-one (CI45350; Acid Yellow No. 73; D&C Yellow No. 8), 5-[(2,4-dinitrophenyl)amino]-2-phenylamino-sodium benzenesulfonate (CI10385; Acid Orange No. 3), 4-[(2,4-dihydroxyphenyl)azo]-monosodium benzenesulfonate (CI14270; Acid Orange No. 6), 4-[(2-hydroxynaphth-1-yl)azo]-sodium benzenesulfonate (CI15510; Acid Orange No. 7), 4-[(2,4-dihydroxy-3-[(2,4-dimethylphenyl)azo]phenyl)azo]-sodium benzenesulfonate (CI20170; Acid Orange No. 24), 4-hydroxy-3-[(4-sulfonaphth-1-yl)azo]-1-naphthalene-disodium sulfonate (CI14720; Acid Red No. 14), 6-hydroxy-5-[(4-sulfonaphth- 1-yl)azo]-2,4-naphthalene-trisodium disulfonate (CI16255; Ponceau 4R; Acid Red No. 18), 3-hydroxy-4-[(4-sulfonaphth-1-yl)azo]-2,7-naphthalene-trisodium disulfonate (CI16185; Acid Red No. 27), 8-amino-1-hydroxy-2-(phenylazo)-3,6-naphthalene-disodium disulfonate (CI17200; Acid Red No. 33), 5-(acetylamino)-4-hydroxy-3-[(2-methylphenyl)-azo]-2,7-naphthalene-disodium disulfonate (CI18065; Acid Red No. 35), 2-(3-hydroxy-2,4,5,7-tetraiod-dibenzopyran-6-one-9-yl)-disodium benzoic acid (CI45430; Acid Red No. 51), the internal salt of N-[6-(diethylamino)-9-(2,4-disulfophenyl)-3H-xanthene-3-ylidene]-N-ethylethane aminium hydroxide, sodium (CI45100; Acid Red No. 52), 8-[(4-(phenylazo)-phenyl)azo]-7-naphthol-1,3-disodium disulfonate (CI27290; Acid Red No. 73), 2',4',5',7'-tetrabromo-3',6'-dihydroxyspiro[isobenzofuran-1(3H),9'-[9H]xanthene]-3-one-disodium (CI45380; Acid Red No. 87), 2',4',5',7'-tetrabromo-4,5,6,7-tetrachloro-3',6'-dihydroxyspiro[isobenzofuran-1(3H),9'[9H]xanthene]-3-one-disodium (CI45410; Acid Red N. 92), 3',6'-dihydroxy-4',5'-diiodospiro-[isobenzofuran-1(3H),9' (9H)-xanthene)-3-one-disodium (CI45425; Acid Red No. 95), (2-sulfophenyl)di[4-(ethyl((4-sulfophenyl)methyl)amino)-phenyl]-carbenium-disodium, betaine (CI42090; Acid Blue No. 9; FD&C Blue No. 1), 1,4-bis[(2-sulfo-4-methylphenyl)amino]-9,10-anthraquinone-disodium (CI61570; Acid Green No. 25), the internal salt of bis[4-(dimethylamino)-phenyl]-(3,7-disulfo-2-hydroxy-naphth-1-yl)carbenium, monosodium (CI44090; Food Green No. 4; Acid Green No. 50), the internal salt of bis[4-(diethylamino)phenyl](2,4-disulfophenyl)-carbenium, sodium (2:1) (CI42045; Food Blue No. 3; Acid Blue No. 1), the internal salt of bis[4-(diethylamino)phenyl](5-hydroxy-2,4-disulfophenyl)-carbenium, calcium salt (2:1) (CI42051; Acid Blue No. 3), 1-amino-4-(cyclohexylamino)-9,10-anthraquinone-2-sodium sulfonate (CI62045; Acid Blue No. 62), 2-(1,3-dihydro-3-oxo-5-sulfo-2H-indole-2-ylidene)-2,3-dihydro-3-oxo-1H-indole-5-disodium sulfonate (CI73015; Acid Blue No. 74), the internal salt of 9-(2-carboxyphenyl)-3-[(2-methylphenyl)-amino]-6-[(2-methyl-4-sulfophenyl)amino]xanthylium, monosodium (CI45190; Acid Violet No. 9), 1-hydroxy-4-[(4-methyl-2-sulfophenyl)amino]-9,10-anthraquinone sodium (CI60730; D&C Violet No. 2; Acid Violet No. 43), bis[3-nitro-4-[(4-phenylamino)-3-sulfo-phenylamino]-phenyl]-sulfone (CI10410; Acid Brown No. 13), 5-amino-4-hydroxy-6-[(4-nitrophenyl)azo]-3-(phenylazo)-2,7-naphthalene disodium disulfonate (CI20470; Acid Black No. 1), 3-hydroxy-4-[(2-hydroxynaphth-1-yl)azo]-7-nitro-1-naphthalene sulfonate chromium complex (3:2) (CI15711; Acid Black No. 52), 3-[(2,4-dimethyl-5-sulfophenyl)azo]-4-hydroxy-1-naphthalene disodium sulfonate (CI14700; Food Red No. 1; Ponceau SX; FD&C Red No. 4), 4-(acetylamino)-5-hydroxy-6-[(7-sulfo-4-[(4-sulfophenyl)azo]naphth-1-yl)azo]-1,7-naphthalene tetrasodium disulfonate (CI28440; Food Black No. 1) and 3-hydroxy-4-(3-methyl-5-oxo-1-phenyl-4,5-dihydro-1H-pyrazole-4-ylazo)-naphthalene-1-sodium sulfonate chromium complex (Acid Red No. 195).

The preferred cationic dyes include, for example, 9-(dimethylamino)-benzo[a]phenoxazine-7-ium-chloride (CI51175; Basic Blue No. 6), di[4-(diethylamino)phenyl][4-(ethylamino)naphthyl]carbenium chloride (CI42595; Basic Blue No. 7), 3,7-di(dimethylamino)phenothiazine-5-ium-chloride (CI52015; Basic Blue No. 9), di[4-(dimethylamino)phenyl][4-(phenylamino)naphthyl]carbenium-chloride (CI44045; Basic Blue No. 26), 2-[(4-(ethyl(2-hydroxyethyl)amino)phenyl)azo]-6-methoxy-3-methyl-benzothiazolium-methylsulfate (CI11154; Basic Blue No. 41), 8-amino-2-bromo-5-hydroxy-4-imino-6-[(3-(trimethylammonio)phenyl)amino]-1(4H)-naphthalenone chloride (CI56059; Basic Blue No. 99), bis[4-(dimethylamino)-phenyl][4-(methylamino)phenyl]carbenium chloride (CI42535; Basic Violet No. 1), tris(4-amino-3-methylphenyl)-carbenium chloride (CI42520; Basic Violet No. 2), tris[4-(dimethylamino)phenyl]carbenium-chloride (CI42555; Basic Violet No. 3), 2-[3,6-(diethylamino)dibenzopyranium-9-yl]-benzoic acid chloride (CI45170; Basic Violet No. 10), di(4-aminophenyl)(4-amino-3-methylphenyl)carbenium-chloride (CI42510; Basic Violet No. 14), 1,3-bis[(2,4-diamino-5-methylphenyl)azo]-3-methylbenzene (CI21010; Basic Brown No. 4), 1-[(4-aminophenyl)azo]-7-(trimethylammonio)-2-naphthol-chloride (CI12250; Basic Brown No. 16), 1-[(4-amino-2-nitrophenyl)azo]-7-(trimethylammonio)-2-naphthol-chloride (CI12251; Basic Brown No. 17), 1-[(4-amino-3-nitro-phenyl)azo]-7-(trimethylammonio)-2-naphthol-chloride (CI12251; Basic Brown No. 17), 3,7-diamino-2,8-dimethyl-5-phenyl-phenazinium-chloride (CI50240; Basic Red No. 2), 1,4-dimethyl-5-[(4-(dimethylamino)phenyl)azo]-1,2,4-triazolium-chloride (CI11055; Basic Red No. 22), 2-hydroxy-1-[(2-methoxy-phenyl)azo]-7-(trimethylammonio)-naphthalene-chloride (CI12245; Basic Red No. 76), 2-[2-((2,4-dimethoxy-phenyl)amino)ethenyl]-1,3,3-trimethyl-3H-indole-1-ium-chloride (CI48055; Basic Yellow No. 11), 3-methyl-1-phenyl-4-[(3-(trimethylammonio)phenyl)-azo]-pyrazole-5-one-chloride (CI12719; Basic Yellow No. 57) and bis[4-(diethylamino)phenyl]phenylcarbenium-hydrogen sulfate (1:1) (CI42040; Basic Green No. 1).

As suitable nonionic dye (especially to improve color leveling and to produce special nuances), the following may be mentioned, for example: 1-amino-2-[(2-hydroxyethyl)amino]-5-nitrobenzene (HC Yellow No. 5), 1-(2-hydroxyethoxy)-2-[(2-hydroxyethyl)-amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitro-phenol, 1-(2-hydroxyethoxy)-3-methylamino-4-nitrobenzene, 2,3-(dihydroxy-propoxy)-3-methylamino-4-nitrobenzene, 2-[(2-hydroxyethyl)amino]-5-nitrophenol (HC Yellow No. 11), 3-[(2-amino-ethyl)amino]-1-methoxy-4-nitrobenzene-hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)-amino]-3-nitrobenzonitrile (HC Yellow No. 14), 4-[(2-hydroxyethyl)amino]-3-nitro-benzamide (HC Yellow No. 15), 1-amino-4-[(2-hydroxyethyl)amino]-2-nitrobenzene (HC Red No. 7), 2-amino-4,6-dinitro-phenol, 2-ethylamino-4,6-dinitrophenol, 4-amino-2-nitro-diphenylamine (HC Red No. 1), 1-amino-4-[di(2-hydroxyethyl)amino]-2-nitrobenzene-hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)-amino]-3-nitrophenol, 1-[(2-aminoethyl)amino]-4-(2-hydroxyethoxy)-2-nitrobenzene (HC Orange No. 2), 4-(2,3-dihydroxy-propoxy)-1-[(2-hydroxy-ethyl)armino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl) amino]-2-nitrobenzene (HC Red No. 11), 2-[(2-hydroxyethyl)amino]-4,6-dinitro-phenol, 4-ethylamino-3-nitrobenzoic acid, 2-[(4-amino-2-nitrophenyl)amino]-benzoic acid, 2-chloro-6-methylamino-4-nitrophenol, 2-chloro-6-[(2-hydroxyethyl)amino]-4-nitrophenol, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzooxazine (HC Red No. 14), 1,4-bis[(2-hydroxyethyl) amino]-2-nitrobenzene, 1-(2-hydroxyethyl)amino-2-nitro-4-[di(2-hydroxyethyl)amino]-benzene (HC Blue No. 2), 1-amino-3-methyl-4-[(2-hydroxyethyl)amino]-6-nitrobenzene (HC Violet No. 1), 4-[ethyl-(2-hydroxyethyl) amino]-1-[(2-hydroxyethyl)amino]-2-nitrobenzene-hydrochloride (HC Blue No. 12), 4-[di(2-hydroxyethyl) amino]-1-[(2-methoxyethyl)amino]-2-nitrobenzene (HC Blue No. 11), 1-[(2,3-dihydroxy-propyl)amino]-4-[methyl-(2-hydroxyethyl)-amino]-2-nitrobenzene (HC Blue No. 10), 1-[(2,3-dihydroxypropyl)amino]-4-[ethyl-(2-hydroxyethyl) amino]-2-nitrobenzene-hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-((4-amino-2-nitrophenyl)amino)-5-dimethyl-amino-benzoic acid (HC Blue No. 13), 1,4-di[(2,3-dihydroxypropyl)amino]-9,10-anthraquinone, 1-[(2-hydroxyethyl)amino]-4-methylamino-9,10-anthraquinone (CI61505, Disperse Blue No. 3), 2-[(2-aminoethyl)amino]-9,10-anthraquinone (HC Orange No. 5), 1-hydroxy-4-[(4-methyl-2-sulfo-phenyl)amino]-9,10-anthraquinone, 1-[(3-aminopropyl)amino]-4-methyl-amino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI62015, Disperse Red No. 11, Solvent Violet No. 26), 1,4-dihydroxy-5,8-bis[(2-hydroxyethyl) amino]-9,10-anthraquinone (CI62500, Disperse Blue No. 7, Solvent Blue No. 69), 1-[di(2-hydroxyethyl)amino]-3-methyl-4-[(4-nitrophenyl)azo]-benzene (CI11210, Disperse Red No. 17), 4-[(4-amino-phenyl)azo]-1-[di(2-hydroxyethyl)amino]-3-methylbenzene (HC Yellow No. 7), 2,6-diamino-3-[(pyridine-3-yl)azo]-pyridine, 2-((4-(acetylamino)phenyl)-azo)-4-methylphenol (CI11855; Disperse Yellow No. 3).

Of the group of substantive dyes, the following are mentioned especially: 2-amino-4,6-dinitrophenol, 2-ethylamino-4,6-dinitrophenyl, 2-((2-hydroxy-ethyl) amino)-4,6-dinitrophenol and dyes of the general formula (IV)

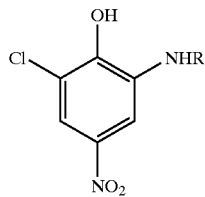

(IV)

in which R is hydrogen, methyl, ethyl, or hydroxymethyl.

The total concentration of substantive dye in the inventive agent is about 0.1 to 10 percent by weight and preferably 0.1 to 5 percent by weight.

Of course, if the coupler and developer substances, as well as the other components of the dye are bases, they can also be used in the form of their physiologically tolerated salts with organic or inorganic acids, such as hydrochloric acid or sulfuric acid. On the other hand, if they have aromatic OH groups, they can be used in the form of salts with bases, such as alkali phenolates.

The above-described, inventive combinations of compounds of Formula (I) with oxidative hair dye precursors (developer and coupler substances) and/or substantive dyes, are applied in a suitable dye carrier composition for the dyeing.

Moreover, the dyeing agents may contain other conventional additives, for example, antioxidants such as ascorbic acid, thioglycolic acid or sodium sulfite, as well as perfume oils, penetrants, buffer systems, complexing agents, preservatives, wetting agents, emulsifiers, thickeners and care materials.

The inventive dyeing agent may be prepared in the form of a solution, particularly an aqueous or aqueous-alcoholic solution. However, a cream, a gel or an emulsion is particularly preferred form of preparation. Their composition represents a mixture of dye components with additives, which are customary for such preparations.

Customary additives for solutions, creams, emulsions or gels are, for example, solvents, such as water, low molecular weight aliphatic alcohols, such as ethanol, propanol or isopropanol, glycerin or glycols, 1,2-propylene glycol, moreover, wetting agents or emulsifiers from the classes of anionic, cationic, amphoteric or nonionic surface active substances, such as fatty alcohol sulfates, ethoxylated fatty alcohol sulfates, alkyl sulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore, thickeners, such as higher molecular weight fatty alcohols, starch, cellulose derivatives, petrolatum, paraffin oil and fatty acids, as well as care materials, such as cationic resins, lanolin derivatives, cholesterol, pantothenic acid and betaine. The components mentioned are used in amounts customary for such purposes. For example, the wetting agents and emulsifiers are used in concentrations of about 0.1 to 30 percent by weight, the thickeners in an amount of about 0.1 to 30 percent by weight and the care materials in a concentration of about 0.1 to 5.0 percent by weight.

The ready-for-use, inventive dyeing agent is prepared by mixing the dye carrier compositions with an oxidizing agent directly before use.

As oxidizing agent, mainly hydrogen peroxide or its addition compounds with urea, melamine, sodium borate or sodium carbonate in the form of a 1 to 12 percent, preferably a 3 to 6 percent, aqueous solution come into consideration. The ratio by weight of hair dyeing agent to oxidizing agent preferably is about 5:1 to 1:3 and particularly 1:1 to 1:2 here. Larger amounts of oxidizing agents are used especially for higher dye concentrations in the hair-dyeing agent or if the hair is to be bleached more at the same time. In principle, however, instead of the aforementioned oxidizing agent, it is also possible to use oxygen from the air to oxidize the dye.

When the dye carrier composition (the pH of which is about 6 to 11.5) is mixed with the mostly acidic oxidizing agent (the pH of which is about 2 to 6.5), the pH of the ready-for-use hair-dyeing agent adjusts itself to a value, which is determined by the amount of alkali in the dye carrier composition and the amount of acid in the oxidizing agent, as well as by the mixing ratio. Depending on the composition, the inventive dyeing agent is weakly acidic, neutral or alkaline and, in the ready-for-use state, has a pH of about 3 to 11 and preferably of about 5 to 10. The adjustment to a basic pH is made preferably with ammonia.

However, organic amines, such as 2-amino-2-methyl-1-propanol, tris(hydroxymethyl)amino-methane, monoethanolamine and triethanolamine, or also inorganic bases, such as sodium hydroxide and potassium hydroxide may also be used. For adjusting the pH to an acidic range, inorganic or organic acids, such as phosphoric acid, acetic acid, lactic acid, ascorbic acid, citric acid or tartaric acid come into consideration.

Subsequently, an amount of this mixture, which depends on the fullness of the hair, is sufficient to dye it and generally is about 60 to 200 gram, is applied on the hair and allowed to act for about 10 to 45 minutes and preferably 30 minutes at 10° to 50° C. and preferably at 30° to 40° C., after which the hair is rinsed with water and dried. Optionally, at the end of this rinsing, the hair is washed with a shampoo and possibly given another rinse with a weak organic acid, such as citric or tartaric acid. Subsequently, the hair is dried.

The inventive hair dyeing agents, which contain diaminopyrazole derivatives of Formula (I) as developer substance, make hair dyeings possible, with outstanding color fastness, especially as far as the light fastness, laundering fastness and resistance to crocking are concerned. With regard to the dyeing characteristics, the inventive dyeing agents, depending on the nature and composition of the dye components, offer a wide palette of different color nuances, which extend from blond over brown, purple, violet to blue and black color shades. Pure red shades are also possible. The color shades are distinguished particularly by their high color intensity. The very good dyeing properties of the inventive hair dyeing agents are furthermore distinguished in that they permit tinting of gray, chemically not damaged hair without any problems and with a good covering power.

The following examples are intended to explain the object of the invention in greater detail, without limiting it.

EXAMPLES

Example 1

Synthesis of 5-Aminomethyl-2H-pyrazole-3,4-diamines

General Procedure

A. Synthesis of Ethyl t-Butyl 2-(4,5-bis-t-Butoxycarbonylamino-pyrazole-1-yl) Carbonate 4,5-Diamino-1-(2-hydroxyethyl)pyrazole sulfate (9.6 g, 0.04 moles), 11.2 mL of triethylamine and 26.3 g (0.12 moles) of di-t-butyl dicarbonate were dissolved in 500 nL of tetrahydrofuran. The reaction mixture is refluxed for 58 hours, subsequently cooled and filtered through a layer of $SiO_2$. The filtrate is then evaporated and the residue chromatographed on $SiO_2$ with a 1:3 mixture of ethyl acetate and hexane.

Ethyl, t-butyl 2-(4,5-bis-t-butoxycarbonylamino-pyrazole-1-yl)(-carbonate) is obtained in an amount of 8 g (45% of the theoretical).

$^1$H-NMR (300 MHz, CDCL3): δ=7.76 (br,s, 1H); 6.91 (br,s, 1H); 6.51 (br,s, 1H); 4.35 (m, 2H); 4.28 (m, 2H); 1.51–1.47 (m, 27H)

B. Synthesis of t-Butyl [4-t-Butoxycarbonylamino-2-isopropyl-2H-pylazole-3-yl]-carbamate 4,5-Diamino-1-isopropyl-pyrazole sulfate (9.5 g, 0.04 moles) and 17.5 g (0.08 moles) of di-t-butyl dicarbonate are dissolved in a mixture of 50 mL of 2N sodium hydrogen carbonate and 120 mL of acetonitrile. The reaction mixture is stirred for 6 hours, then poured into water and extracted twice with 100 mL of ethyl acetate. The combined extracts are evaporated and the residue taken up in 200 mL of hexane. The precipitate is filtered off and washed with 50 mL of hexane.

t-Butyl [4-t-butoxycarbonylamino-2-isopropyl-ethyl)-2H-pyrazole-3-yl]-carbamate is obtained in an amount of 10 g (73% of the theoretical).

$^1$H-NMR (300 MHz, CDCL3): δ=7.48 (s, 1H); 6.35 (br,s, 1H); 6.10 (br,s, 1H); 4.23 (sp, 1H); 1.50 (s, 9H); 1.49 (s, 9H); 1.44 (d, 6H)

C. Synthesis of t-Butylester of [5-Bromo-4-t-butoxycarbonylamino-2-(2-hydroxyethyl)-2H-pyrazole-3-yl]-carbamate To a solution of 4.25 g (0.09 moles) of t-butyl 2-(4,5-bis-t-butoxycarbonyl-amino-pyrazole-1-yl) carbonate from step A, a solution of 2.13 g of N-bromo-succinimide (0.1 moles) in 40 mL of tetrahydrofuran is added dropwise at room temperature. The reaction mixture is stirred for 3.5 hours at room temperature and then poured into a mixture of 100 mL of aqueous $Na_2S_2O_3$ solution and 100 mL of ethyl acetate. The aqueous phrase is extracted with ethyl acetate and the combined organic phases are then washed with saturated sodium chloride solution, dried and evaporated. The residue is taken up in a mixture of 15 mL of methanol, 50 mL of hexane and 15 mL of water and cooled to 4° C. Subsequently, the reaction mixture is treated in portions with 10 equivalents of lithium hydroxide, stirred overnight at room temperature and then poured into a 1:1 mixture of a 5% aqueous sodium hydrogen phosphate solution and ethyl acetate. The organic phase is dried and evaporated and the residue is chromatographed on silica with a 1:1 to 2:1 gradient of ethyl acetate and hexane. t-Butyl [4-t-butoxycarbonylamino-5-bromo-2-isopropyl-2H-pyrazole-3-yl] carbamate was obtained in a yield of 3.3 g (78% of the theoretical).

$^1$H-NMR (300 MHz, CDCL3): δ=7.19 (br,s, 1H); 6 (br,s, 1H); 4.12 (m, 2H); 3.99 (m, 2H); 2.04 (s, 1H); 1.50 (s, 9H); 1.49 (s, 9H)

D. Synthesis of t-Butyl [4-t-Butoxycarbonylamino-5-bromo-2-isopropyl-2H-pyrazole-3-yl] carbamate To a solution of 5.5 g (0.016 moles of t-butyl 4-t-butoxycarbonyl-amino-2-isopropyl-2H-pyrazole-3-yl carbamate from step B, a solution of 3.5 g (0.02 moles) of N-bromo-succinimide in 40 mL of tetrahydrofuran is added at room temperature. The reaction mixture is stirred for 3.5 hours at room temperature and then poured into a mixture of 100 mL of aqueous $Na_2S_2O_3$ solution and 100 mL of ethyl acetate. The aqueous phrase is extracted with ethyl acetate and the combined organic phases are then washed with saturated sodium chloride solution, dried and evaporated. The residue is suspended in a 100 mL of a 1:1 mixture of diethyl ether and hexane, filtered and dried. t-Butyl [4-t-butoxycarbonylamino-5-bromo-2-isopropyl-2H-pyrazole-3-yl] carbamate is obtained in a yield of 6 g (89% of the theoretical).

$^1$H-NMR (300 MHz, CDCL3): δ=6.77 (br,s, 1H); 5.95 (br,s, 1H); 4.46 (sp, 1H); 1.50 (s, 9H); 1.49 (s, 9H); 1.44 (d, 6H)

E. Synthesis of t-Butyl [4-t-Butoxycarbonylamino-5-formyl-2-isopropyl-2H-pyrazole-3-yl] carbamate The t-butyl ester of [4-t-butoxycarbonylamino-5-bromo-2-isopropyl-2H-pyrazole-3-yl] carbamate (3.7 g, 0.01 moles) from step D is dissolved under argon in 100 mL of anhydrous tetrahydrofuran and 17 mL of a 1.6 M solution of methyl lithium in ether (0.03 moles) are added stepwise. The reaction mixture is cooled to −78° C. and treated stepwise with 7 mL of a 1.5 M solution of t-butyl lithium (0.01 moles). At the end of the addition, the solution is stirred for a further 30 minutes at the given temperature. Subsequently, 1.2 g (0.02 moles) of dimethylformamide are added and the reaction mixture stirred for 1 hour at −78° C., allowed to warm up slowly to room temperature, hydrolyzed with water and then poured into diethyl ether. The aqueous phase is extracted with diethyl ether and the combined organic phases are then dried with magnesium sulfate. The solvent is distilled off on the rotary evaporator and the residue purified with a 9:1 mixture of petroleum and ethyl acetate on silica gel.

$^1$H-NMR (300 MHz, CDCL3): δ=9.86 (s, 1H); 7.57 (br,s, 1H); 7.33 (br,s, 1H); 4.61 (sp, 1H); 1.50 (s, 9H); 1.49 (s, 9H); 1.47 (d, 6H)

F. Synthesis of t-Butyl [4-t-Butoxycarbonylamino-5-formyl-2-(2-hydroxyethyl)-2H-pyrazole-3-yl]-carbamate The t-butyl ester of [5-bromo-4-t-butoxycarbonylamino-2-(2-hydroxyethyl)-2H-pyrazole-3-yl] carbamate (4.21 g, 0.01 moles) from step C. is dissolved under argon in 100 mL of anhydrous tetrahydrofuran and 17 mL of a 1.6 M solution of methyl lithium in ether (0.03 moles) are added stepwise. The reaction mixture is cooled to −78° C. and treated stepwise with 7 mL of 1.5 M solution of t-butyl lithium (0.01 moles). At the end of the addition, the solution is stirred for a further 30 minutes at the given temperature. Subsequently, 1.2 g (0.02 moles) of dimethylformamide are added and the reaction mixture stirred for 1 hour at −78° C., allowed to warm up slowly to room temperature, hydrolyzed with water and then poured into diethyl ether. The aqueous phase is extracted with diethyl ether and the combined organic phases are then dried with magnesium sulfate. The solvent is distilled off on the rotary evaporator and the residue purified with a 9:1 mixture of petroleum and ethyl acetate on silica gel.

$^1$H-NMR (300 MHz, CDCL3): δ=9.86 (s, 1H); 7.6 (br,s, 2H); 4.29 (m, 2H); 4.10 (m, 2H); 1.50 (s, 9H); 1.50 (s, 9H); 1.48 (d, 6H)

G. Synthesis of 5-Aminomethyl-2H-pyrazole-3,4-diamines

The aldehyde derivatives (0.0001 moles) from step E or F and 0.00015 moles of the corresponding amine are dissolved in 1,2-dichloroethane. Subsequently 0.1 mL of an acetic acid solution (1 M in 1,2-dichloroethane) and 0.06 g of NaBH(OAc)$_3$ (0.0003 moles) are added and the reaction mixture is stirred 5 to 15 hours at room temperature. At the end of the reaction, the reaction mixture is poured into 10 mL of ethyl acetate and the organic phase is extracted with sodium hydrogen carbonate and then dried with magnesium sulfate. The solvent is evaporated in a rotary evaporator and the residue purified on silica gel with a 9:1 mixture of petroleum ether and ethyl acetate. The product, so obtained, is heated in 4 mL of ethanol to 50° C. Subsequently, for the preparation of the hydrochloride, 1.5 mL of a 2.9 M ethanolic solution of hydrochloric acid is added dropwise. The precipitate is filtered off, washed twice with I mL of methanol and then dried.

a. 4-{[4,5-Diamino-1-(2-hydroxyethyl)-1H-pyrazole-3-ylmethyl]-amino}-phenol*HCl

Aldehyde derivative used: of Step F
Amine used: 4-amino-phenol
Mass spectrum: MH$^+$ 264 (100)

b. 2-{4,5-Diamino-3-[(4-amino-phenylamino)-methyl]-pyrazole-1-yl}-ethanol*HCl

Aldehyde derivative used: of Step F
Amine used: 1,4-diaminobenzene
Mass spectrum: MH$^+$ 263 (100)

c. 2-(4,5-Diamino-3-phenylaminomethyl-pyirazole-1-yl)-ethanol*HCl

Aldehyde derivative used: of Step F
Amine used: 1,3-diaminobenzene
Mass spectrum: MH$^+$ 248 (100)

d. 2-Isopropyl-5-phenylaminomethyl-2H-pyrazole-3,4-diamine*HCl

Aldehyde derivative used: of Step F
Amine used: aniline
Mass spectrum: MH$^+$ 246 (100)

e. 2-{4,5-Diamino-3-[(3-amino-phenylamino)-methyl]-pyrazole-1-yl}-ethanol*HCl

Aldehyde derivative used: of Step F
Amine used: 1,3-diaminobenzene
Mass spectrum: MH$^+$ 263 (100)

f. 2-{4,5-Diamino-3-[(4-amino-2-methyl-phenylamino)-methyl]-pyrazole-1-yl}-ethanol*HCl and 2-{4,5-diamino-3-[(4-amino-3-methyl-phenylamino)-methyl]-pyrazole-1-yl}-ethanol*HCl Aldehyde derivative used: of Step F
Amine used: 2,5-diamino-toluene
Mass spectrum: MH$^+$ 277 (100)

g. 2-(4,5-Diamino-3-{[4-amino-2-(2-hydroxyethyl)-phenylamino]-methyl}-pyrazole-1-yl)-ethanol*HCl and 2-(4,5-diamino-3-{[4-amino-3-(2-hydroxyethyl)-phenylamino]-methyl}-pyrazole-1-yl)-ethanol*HCl Aldehyde derivative used: of Step F
Amine used: 2-(2,5-diamino-phenyl)-ethanol
Mass spectrum: MH$^+$ 307 (100)

h. 2-{4,5-Diamino-3-[(4-dimethylamino-phenylamino)-methyl]-pyrazole-1-yl}-ethanol*HCl Aldehyde derivative used: of Step F
Amine used: 4-dimethylamino-aniline
Mass spectrum: MH$^+$ 291 (100)

i. 2-[4,5-Diamino-3-(benzo[1,3]dioxol-5-ylaminomethyl)-pyrazole-1-yl]-ethanol*HCl Aldehyde derivative used: of Step F
Amine used: benzo[1,3]dioxol-5-ylamine
Mass spectrum: MH$^+$ 292 (100)

j. 4-Chloro-2-{[4,5-diamino-1-(2-hydroxyethyl)-1H-pyrazole-3-ylmethyl]-amino}phenol*HCl Aldehyde derivative used: of Step F
Amine used: 2-amino-4-chloro-phenol
Mass spectrum: MH$^+$ 297 (100)

k. 3-{[4,5-Diamino-1-(2-hydroxyethyl)-1H-pyrazole-3-ylmethyl]-amino}phenol*HCl

Aldehyde derivative used: of Step F
Amine used: 3-amino-phenol
Mass spectrum: MH$^+$ (100)

l. 5-{[4,5-Diamino-1-(2-hydroxyethyl)-1H-pyrazole-3-ylmethyl]-amino}2-methyl-phenol*HCl Aldehyde derivative used: of Step F
Amine used: 5-amino-2-methyl-phenol Mass spectrum: MH⁺ 264 (100)
m. 2-{4,5-Diamino-3-[(3,4-dimethoxy-phenylamino)-methyl]-pyrazole-1-yl}-ethanol*HCl
   Aldehyde derivative used: of Step F
   Amine used: 3,4-dimethoxy-aniline
   Mass spectrum: MH⁺ 308 (100)
n. 2-{[4,5-Diamino-1-(2-hydroxyethyl)-1H-pyrazole-3-ylmethyl]-amino}-4-nitrophenol*HCl
   Aldehyde derivative used: of Step F
   Amine used: 2-amino-4-nitro-phenol
   Mass spectrum: MH⁺ 309 (100)
o. 4-[(4,5-Diamino-1-isopropyl-1H-pyrazole-3-ylmethyl)-amino]-phenol*HCl
   Aldehyde derivative used: of Step E
   Amine used: 4-amino-phenol
   Mass spectrum: MIH⁺ 262 (100)
p. 3-[(4,5-Diamino-1-isopropyl-1H-pyrazole-3-ylmethyl)-amino]-phenol*HCl
   Aldehyde derivative used: of Step E
   Amine used: 3-amino-phenol
   Mass spectrum: MH⁺ 262 (100)
q. 5-[(4,5-Diamino-1-isopropyl-1H-pyrazole-3-ylmethyl)-amino]-2-methyl-phenol*HCl
   Aldehyde derivative used: of Step E
   Amine used: 5-amino-2-methyl-phenol
   Mass spectrum: MH⁺ (100)
r. 5-[(3,4-Dimethoxy-phenylamino)-methyl]-2-isopropyl-2H-pyrazole-3,4-diamine*HCl
   Aldehyde derivative used: of Step E
   Amine used: 3,4-dimethoxy-aniline
   Mass spectrum: MH⁺ 306 (100)
s. 2-[(4,5-Diamino-1-isopropyl-1H-pyrazole-3-ylmethyl)-amino]-4-nitro-phenol*HCl
   Aldehyde derivative used: of Step E
   Amine used: 2-arnino-4-nitro-phenol
   Mass spectrum: MH⁺ 306 (40)
t. 5-[(3-Amino-phenylamino)-methyl]-2-isopropyl-2H-pyrazole-3,4-diamine*HCl
   Aldehyde derivative used: of Step E
   Amine used: 1,3-diaminobenzene
   Mass spectrum: MH⁺ 261 (100)
u. 5-[(4-Amino-phenylamino)-methyl]-2-isopropyl-2H-prazole-3,4-diamine*HCl
   Aldehyde derivative used: of Step E
   Amine used: 1,4-diaminobenzene
   Mass spectrum: MH⁺ 261 (100)
v. 5-[(4-Amino-2-methyl-phenylamino)-methyl]-2-isopropyl-2H-pyrazole-3,4-diamine*HCl and 5-[(4-amino-3-methyl-phenylamino)-methyl]-2-isopropyl-2H-pyrazole-3,4-diamine*HCl
   Aldehyde derivative used: of Step E
   Amine used: 2,5-diamino-toluene
   Mass spectrum: MH⁺ 275 (100)
w. 2-{5-Amino-2-[(4,5-diamino-1-isopropyl-1H-prazole-3-ylmethyl)-amino]-phenyl}-ethanol*HCl and 2-{6-amino-3-[(4,5-diamino-1-isopropyl-1H-prazole-3-ylmethyl)-amino]-phenyl}-ethanol*HCl
   Aldehyde derivative used: of Step E
   Amine used: 2-(2,5-diamino-phenyl)-ethanol
   Mass spectrum: MH⁺ 305 (100)
x. 2-{4-Amino-2-[(4,5-diamino-1-isopropyl-1H-pyrazole-3-ylmethyl)-amino]-phenoxy}-ethanol*HCl
   Aldehyde derivative used: of Step E
   Amine used: 2-(2,4-diamino-phenoxy)-ethanol
   Mass spectrum: MH⁺ 321 (100)
y. 5-[(4-Dimethylamino-phenylamino)methyl]-2-isopropyl-2H-pyrazole-3,4-diamine*HCl
   Aldehyde derivative used: of Step E
   Amine used: 4-dimethylamino-aniline
   Mass spectrum: MH⁺ 289 (100)

Examples 2 to 26

Hair Dyeing Agent

Hair dye solutions of the following composition are prepared:

| | |
|---|---|
| 1.25 mmoles | developer substance of Formula (I) of Table 1 |
| 1.25 mmoles | coupler substance of Table 1 |
| 1.0 g | potassium oleate (8% aqueous solution) |
| 1.0 g | ammonia (22% aqueous solution) |
| 1.0 g | ethanol |
| 0.3 g | ascorbic acid |
| ad 100.0 g | water |

The above dye solution (50 g) is mixed immediately before use with 50 g of a 6% aqueous hydrogen peroxide solution. Subsequently, the mixture is applied on bleached hair. After a period of action of 30 minutes at 40° C., the hair is rinsed with water, washed with a conventional shampoo and dried. The resulting dyeings are summarized in Table 1.

TABLE 1

| | | Coupler Substance | | |
|---|---|---|---|---|
| Example No. | Developer Substance of Formula (I) | I. 3-amino-2-chloro-6-methyl-phenol | II. 1,3-diamino-4-(2-hydroxy-ethoxy)-benzene sulfate | III. 5-amino-2-methyl-phenol | IV. 1-naphthol |
| 2. | of Example 1a | red | violet | orange | light orange |
| 3. | of Example 1b | violet | blue | claret | gray red |
| 4. | of Example 1c | violet | blue violet | red | orange |
| 5. | of Example 1d | violet | blue violet | red | orange |
| 6. | of Example 1e | violet | blue | claret | gray red |
| 7. | of Example 1f | violet | blue | claret | gray red |
| 8. | of Example 1g | violet | blue | claret | gray red |
| 9. | of Example 1h | light violet | light blue | claret | gray red |
| 10. | of Example 1i | violet | blue violet | red | orange |

TABLE 1-continued

| Example No. | Developer Substance of Formula (I) | Coupler Substance | | | |
|---|---|---|---|---|---|
| | | I. 3-amino-2-chloro-6-methyl-phenol | II. 1,3-diamino-4-(2-hydroxy-ethoxy)-benzene sulfate | III. 5-amino-2-methyl-phenol | IV. 1-naphthol |
| 11. | of Example 1j | light violet | light blue | claret | gray red |
| 12. | of Example 1k | light violet | light blue | claret | gray red |
| 13. | of Example 1l | light violet | light blue | claret | gray red |
| 14. | of Example 1m | light violet | light blue | red | gray red |
| 15. | of Example 1n | red | brown | orange | orange |
| 16. | of Example 1o | red | violet | orange | light orange |
| 17. | of Example 1p | violet | violet blue | claret | orange |
| 18. | of Example 1q | light violet | light blue | claret | orange |
| 19. | of Example 1r | light violet | light blue | claret | orange |
| 20. | of Example 1s | light violet | light blue | claret | orange |
| 21. | of Example 1t | light violet | light blue | claret | orange |
| 22. | of Example 1u | violet | blue | light violet | Gray |
| 23. | of Example 1v | violet | blue | light violet | gray |
| 24. | of Example 1w | violet | blue | light violet | gray |
| 25. | of Example 1x | light violet | light blue | light violet | gray |
| 26. | of Example 1y | light violet | light blue | light violet | gray |

Examples 27 to 38

Hair Dyeing Agent

Hair dyeing solutions of the following composition are prepared:

| | |
|---|---|
| X g | developer E1 to E2 of Formula (I) of Table 2 |
| U g | developer E8 to E15 of Table 2 |
| Y g | coupler substance K11 to K36 of Table 4 |
| 10.0 g | potassium oleate (8% aqueous solution) |
| 10.0 g | ammonia (22% aqueous solution) |
| 10.0 g | ethanol |

-continued

| | |
|---|---|
| 0.3 g | ascorbic acid |
| ad 100.0 g | water |

The above dye solution (30 g) is mixed immediately before use with 30 g of a 6% aqueous hydrogen peroxide solution. Subsequently, the mixture is applied on bleached hair. After a period of action of 30 minutes at 40° C., the hair is rinsed with water, washed with a conventional shampoo and dried. The resulting dyeings are summarized in Table 5.

Examples 39 to 50

Hair Dyeing Agent

Creamy dye carrier compositions with the following components are prepared:

| | |
|---|---|
| X g | developer substance E3 to E6 of Formula (I) of Table 2 |
| U g | developer substance E8 to E15 of Table 2 |
| Y g | coupler substance K11 to K36 of Table 4 |
| Z g | direct dye D2 of Table 3 |
| 15.0 g | cetyl alcohol |
| 0.3 g | ascorbic acid |
| 3.5 g | sodium lauryl alcohol diglycol ether sulfate, 28% aqueous solution |
| 3.0 g | ammonia, 22% aqueous solution |
| 0.3 g | sodium sulfite, water-free |
| ad 100.0 g | water |

The above dye cream (30 g) is mixed immediately before use with 30 g of a 6% aqueous hydrogen peroxide solution. Subsequently, the mixture is applied on bleached hair. After a period of action of 30 minutes at 40° C., the hair is rinsed with water, washed with a conventional shampoo and dried. The resulting dyeings are summarized in Table 6.

TABLE 2

| | Developer Substance |
|---|---|
| E1 | 4-{[4,5-diamino-1-(2-hydroxy-ethyl)-1H-pyrazole-3-ylmethyl]-amino}-phenol*HCl |
| E2 | 4-[(4,5-diamino-1-isopropyl-1H-pyrazole-3-ylmethyl)-amino]-phenol*HCl |
| E3 | 2-{4,5-diamino-3-[(4-amino-phenylamino)-methyl]-pyrazole-1-yl}-ethanol*HCl |
| E4 | 5-[(4-amino-phenylamino)-methyl]-2-isopropyl-2H-pyrazole-3,4-diamine*HCl |
| E5 | 2-isopropyl-5-phenylaminomethyl-2H-pyrazole-3,4-diamine*HCl |
| E6 | 2-(4,5-diamino-3-phenylaminomethyl-pyrazole-1-yl)-ethanol*HCl |
| E8 | 1,4-diaminobenzene |
| E9 | 2,5-diamino-phenylethanol sulfate |
| E10 | 3-methyl-4-amino-phenol |
| E11 | 4-amino-2-aminomethyl-phenol-dihydrochloride |
| E12 | 4-amino-phenol |
| E13 | N,N-bis(2'-hydroxyethyl)-p-phenylenediamine sulfate |
| E14 | 4,5-diamino-1-(2'-hydroxyethyl)-pyrazole sulfate |
| E15 | 2,5-diaminotoluene sulfate |

TABLE 3

| | Substantive Dyes |
|---|---|
| D1 | 2,6-diamino-3-((pyridine-3-yl)azo)pyridine |
| D2 | 6-chloro-2-ethylamino-4-nitrophenol |
| D3 | 2-amino-6-chloro-4-nitrophenol |

TABLE 4

Coupler Substances

| | |
|---|---|
| K11 | 1,3-diaminobenzene |
| K12 | 2-amino-4-(2'-hydroxyethyl)amino-anisole sulfate |
| K13 | 1,3-diamino-4-(2'-hydroxyethoxy)benzene sulfate |
| K14 | 2,4-diamino-5-fluoro-toluene sulfate |
| K15 | 3-amino-2-methylamino-6-methoxy-pyridine |
| K16 | 3,5-diamino-2,6-dimethoxy-pyridine-dihydrochloride |
| K17 | 2,4-diamino-5-ethoxy-toluene sulfate |
| K18 | N-(3-dimethylamino)phenylurea |
| K19 | 1,3-bis(2,4-diaminophenoxy)propane-tetrahydrochloride |
| K21 | 3-amino-phenol |
| K22 | 5-amino-2-methyl-phenol |
| K23 | 3-amino-2-chloro-6-methyl-phenol |
| K24 | 5-amino-4-fluoro-2-methyl-phenol sulfate |
| K25 | 1-naphthol |
| K26 | 1-acetoxy-2-methyl-naphthalene |
| K31 | 1,3-dihydroxy-benzene |
| K32 | 2-methyl-1,3-dihydroxy-benzene |
| K33 | 1-chloro-2,4-dihydroxy-benzene |
| K34 | 4-(2'-hydroxyethyl)amino-1,2-methylenedioxybenzene hydrochloride |
| K35 | 3,4-methylenedioxy-phenol |
| K36 | 2-amino-5-methyl-phenol |

TABLE 5

Hair-Dyeing Agents

| Example No. | 27 | 28 | 29 | 30 |
|---|---|---|---|---|
| Dye | (amount of dye in grams) | | | |
| E1 | 0.30 | 0.30 | 0.30 | 0.30 |
| E8 | 0.25 | | | |
| E13 | | 0.20 | | |
| E14 | | | | 0.30 |
| E15 | | | 0.20 | 0.30 |
| K22 | 0.30 | 0.30 | | 0.30 |
| K23 | | | 0.35 | |
| K31 | 0.18 | | | 0.20 |
| K32 | | 0.22 | | |
| K33 | | | 0.20 | |
| Dyeing Result | reddish brown | reddish brown | reddish brown | reddish brown |

| Example No. | 31 | 32 | 33 | 34 |
|---|---|---|---|---|
| Dye | (amount of dye in grams) | | | |
| E1 | 0.15 | 0.20 | 0.10 | 0.30 |
| E8 | 0.25 | | | |
| E10 | 0.15 | | | |
| E11 | | 0.10 | | |
| E12 | | | 0.20 | |
| E13 | | 0.20 | | |
| E14 | | | | 0.30 |
| E15 | | | 0.20 | 0.30 |
| K22 | 0.20 | 0.10 | 0.20 | 0.15 |
| K23 | | 0.10 | | 0.15 |
| K25 | 0.10 | 0.10 | | |
| K26 | | | 0.15 | |
| K31 | 0.18 | | | 0.20 |
| K32 | | 0.22 | | |
| K33 | | | 0.20 | |
| Dyeing Result | reddish brown | reddish brown | reddish brown | reddish brown |

| Example No. | 35 | 36 | 37 | 38 |
|---|---|---|---|---|
| Dye | (amount of dye in grams) | | | |
| E2 | 0.30 | 0.30 | 0.30 | 0.30 |
| E8 | 0.25 | | | |
| E13 | | 0.20 | | |
| E14 | | | | 0.30 |
| E15 | | | 0.20 | 0.30 |
| K22 | 0.30 | 0.30 | | 0.30 |
| K23 | | | 0.35 | |
| K31 | 0.18 | | | 0.20 |
| K32 | | 0.22 | | |
| K33 | | | 0.20 | |
| Dyeing Result | reddish brown | reddish brown | reddish brown | reddish brown |

TABLE 6

Hair Dyeing Agents

| Example No. | 39 | 40 | 41 | 42 | 43 | 44 |
|---|---|---|---|---|---|---|
| Dye | (amount of dye in grams) | | | | | |
| E3 | 0.20 | 0.30 | 0.20 | | | |
| E4 | | 0.25 | | | | 0.20 |
| E5 | | | | 0.20 | | |
| E6 | | | | | 0.20 | |
| E8 | 1.60 | | | | | |
| E13 | | 1.80 | | | | |
| E15 | | | 1.60 | 0.50 | 0.50 | 0.50 |
| K12 | | | | 0.10 | 0.10 | 0.10 |
| K13 | 1.10 | 1.10 | 1.10 | | | |
| K23 | | | 0.05 | 0.10 | 0.10 | 0.10 |
| K31 | 1.10 | 1.10 | 1.10 | 0.40 | 0.40 | 0.40 |
| D2 | | | | 0.10 | 0.10 | 0.10 |
| Dyeing Result | black | black | black | brown | brown | brown |

| Example No. | 45 | 46 | 47 | 48 | 49 | 50 |
|---|---|---|---|---|---|---|
| Dye | (amount of dye in grams) | | | | | |
| E3 | 0.20 | | | | 0.30 | |
| E4 | | 0.20 | | | | 0.20 |
| E5 | | | 0.20 | | | |
| E6 | | | | 0.30 | | |
| E15 | 1.80 | 1.80 | 1.80 | 0.30 | 0.50 | 0.60 |
| K12 | | | | 0.10 | 0.10 | 0.10 |
| K13 | 1.10 | 1.10 | 1.10 | | | |
| K23 | | | 0.05 | 0.10 | 0.10 | 0.10 |
| K31 | 1.10 | 1.10 | 1.10 | 0.40 | 0.40 | 0.40 |
| D2 | | | | 0.10 | 0.10 | 0.10 |
| Dyeing Result | black | black | black | brown | brown | brown |

Unless stated otherwise, all percentages in the present application are percentages by weight.

What is claimed is:

1. Diaminiopyrazole derivative of the general Formula (I) or its physiological tolerated, water-soluble salt with inorganic or organic acids

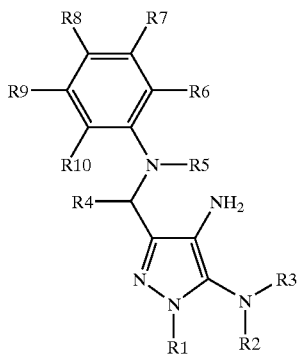

(I)

wherein
- R1 represents a $C_1$–$C_6$ alkyl group, a $C_2$–$C_4$ hydroxyalkyl group, a $C_3$–$C_4$ dihydroxyalkyl group or a $C_2$–$C_6$ alkoxy ($C_1$–$C_2$) alkyl group, a phenyl group, a benzyl group or a substituted benzyl group;
- R2 and R3 independently of one another are hydrogen, a $C_1$–$C_6$ alkyl group, a hydroxy ($C_2$–$C_4$) alkyl group, a dihydroxy ($C_3$–$C_4$) alkyl group or a $C_2$–$C_4$ alkoxy-($C_1$–$C_2$) alkyl group or R2 and R3, together with the nitrogen, form a 4-member to 8-member heteroaliphatic ring;
- R4 represents hydrogen or a $C_1$–$C_6$ alkyl group;
- R5 is hydrogen, a $C_1$–$C_6$ alkyl group, an unsaturated $C_2$–$C_6$ alkyl group, a hydroxy ($C_2$–$C_4$) alkyl group, a dihydroxy ($C_3$–$C_4$) alkyl group, an amino ($C_2$–$C_4$) alkyl group, a dimethylamino ($C_2$–$C_4$) alkyl group, an acetylamino ($C_2$–$C_4$) alkyl group, a methoxy ($C_2$–$C_4$) alkyl group, an ethoxy ($C_2$–$C_4$) alkyl group, a $C_1$–C4 cyanoalkyl group, a carboxy ($C_1$–$C_4$) alkyl group or an aminocarbonyl ($C_1$–$C_4$) alkyl group;
- R6, R7, R8, R9, R10 independently of one another represent hydrogen, a halogen atom (F, Cl Br, I), a cyano group, a hydroxy group, a $C_1$–$C_4$ alkoxy group, a hydroxy ($C_2$–$C_4$) alkoxy group, a $C_1$–$C_6$ alkyl group, a $C_1$–$C_4$ alkylthioether group, a mercapto group, a nitro group, an amino group, a ($C_1$–$C_4$) alkylamino group, a hydroxy ($C_2$–$C_4$) alkylamino group, a di($C_1$–$C_4$) alkylamino group, a di(hydroxy($C_2$–$C_4$)alkyl) amino group, a (dihydroxy($C_3$–$C_4$)alkyl) amino group, a (hydroxy ($C_2$–$C_4$)alkyl)-($C_1$–$C_4$)alkylamino group, a trifluoromethyl group, a —C(O)H group, a —C(O)$CH_3$ group, a —C(O)$CF_3$ group, an —Si$(CH_3)_3$ group, a hydroxy ($C_2$–$C_4$) alkyl group or a dihydroxy($C_3$–$C_4$) alkyl group or two adjacent R6 to R10 groups form an —O—CH2—O—bond.

2. The diaminopyrazole derivative of claim 1, wherein R2 and R3 in Formula (I) represent hydrogen and R1 is a $C_1$–$C_4$ alkyl group, a $C_2$–$C_4$ hydroxyalkyl group, a benzyl group or a methylbenzyl group.

3. The diaminopyrazole derivative of claim 1, wherein R2, R3, R4 and R5 in Formula (I) are hydrogen and R1 is a $C_1$–$C_4$ alkyl group, a $C_2$–$C_4$ hydroxyalkyl group, a benzyl group or a methylbenzyl group.

4. The diaminopyrazole derivative of claim 1, wherein R2, R3, R4 and R5 in Formula (I) are hydrogen and R1 is a $C_1$–$C_4$ alkyl group, a $C_2$–$C_4$ hydroxyalkyl group, a benzyl group or a methylbenzyl group, and at least one of the R6 to R10 groups is a hydroxy group or an amino group, while the remaining R6 to R10 groups are hydrogen.

5. The diaminopyrazole derivative of claim 1, wherein it is selected from 4-{[4,5-diamino-1-(2-hydroxy-ethyl)-1H-pyrazole-3-ylmethyl]-amino}-phenol, 2-{4,5-diamino-3-[(4-amino-phenylamino)-methyl]-pyrazole-1-yl}-ethanol, 2-(4,5-diamino-3-phenylaminomethyl-pyrazole-1-yl)-ethanol, 2-isopropyl-5-phenylaminomethyl-2H-pyrazole-3,4-diamine, 2-{4,5-diamino-3-[(3-amino-phenylamino)-methyl]-pyrazole-1-yl}-ethanol, 2-{4,5-diamino-3-[(4-amino-2-methyl-phenylamino)-methyl]-pyrazole-1-yl}-ethanol, 2-{4,5-diamino-3-[(4-amino-3-methyl-phenylamino)-methyl]-pyrazole-1-yl}-ethanol, 2-(4,5-diamino-3-{[4-amino-2-(2-hydroxyethyl)-phenylamino]-methyl}-pyrazole-1-yl)-ethanol, 2-(4,5-diamino-3-{[4-amino-3-(2-hydroxyethyl)-phenylamino]-methyl}-pyrazole-1-yl)-ethanol, 2-{4,5-diamino-3-[(4-dimethylamino-phenylamino)-methyl]-pyrazole-1-yl}-ethanol, 2-[4,5-diamino-3-(benzo[1,3]dioxol-5-ylaminomethyl)-pyrazole-1-yl]-ethanol, 4-chloro-2-{[4,5-diamino-1-(2-hydroxyethyl)-1H-pyrazole-3-ylmethyl]-amino}-phenol, 3-{[4,5-diamino-1-(2-hydroxyethyl)-1H-pyrazole-3-ylmethyl]-amino}-phenol, 5-{[4,5-diamino-1-(2-hydroxyethyl)-1H-pyrazole-3-ylmethyl]-amino}-2-methyl-phenol, 2-{4,5-diamino-3-[(3,4-dimethoxy-phenylamino)-methyl]-pyrazole-1-yl}-ethanol, 2-{[4,5-diamino-1-(2-hydroxy-ethyl)-1H-pyrazole-3-ylmethyl]-amino}-4-nitro-phenol, 4-[(4,5-diamino-1-isopropyl-1H-pyrazole-3-ylmethyl)-amino]-phenol, 3-[(4,5-diamino-1-isopropyl-1H-pyrazole-3-ylmethyl)-amino]-phenol, 5-[(4,5-diamino-1-isopropyl-1H-pyrazole-3-ylmethyl)-amino]-2-methyl-phenol, 5-[(3,4-dimethoxy-phenylamino)-methyl]-2-isopropyl-2H-pyrazole-3,4-diamine, 2-[(4,5-diamino-1-isopropyl-1H-pyrazole-3-ylmethyl)-amino]-4-nitro-phenol, 5-[(3-amino-phenylamino)-methyl]-2-isopropyl-2H-pyrazole-3,4-diamine, 5-[(4-amino-phenylamino)-methyl]-2-isopropyl-2H-pyrazole-3,4-diamine, 5-[(4-amino-2-methyl-phenylamino)-methyl]-2-isopropyl-2H-pyrazole-3,4-diamine, 5-[(4-amino-3-methyl-phenylamino)-methyl]-2-isopropyl-2H-pyrazole-3,4-diamine, 2-{5-amino-2-[(4,5-diamino-1-isopropyl-1H-pyrazole-3-ylmethyl)-amino]-phenyl}-ethanol, 2-{6-amino-3-[(4,5-diamino-1-isopropyl-1H-pyrazole-3-ylmethyl)-amino]-phenyl}-ethanol, 2-{4-amino-2-[(4,5-diamino-1-isopropyl-1H-pyrazole-3-ylmethyl)-amino]-phenoxy}-ethanol and 5-[(4-dimethylamino-phenylamino)-methyl]-2-isopropyl-2H-pyrazole-3,4-diamine.

6. An agent for the oxidative dyeing of keratin fibers on the basis of a combination of a developer substance and a coupler substance, wherein it contains at least one diaminopyrazole derivative of Formula (I) of claim 1 as developer substance.

7. The agent of claim 6, wherein the diaminopyrazole derivative of Formula (I) is contained in an amount of 0.005 to 20 percent by weight.

8. The agent of claim 6, wherein the coupler substance is selected from N-(3-dimethylamino-phenyl)-urea, 2,6-diamino-pyridine, 2-amino-4-[(2-hydroxyethyl)-amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxy-ethyl)amino]-1,5-dimethoxybenzene, 2,3-diamino-6-methoxy-pyridine, 3-amino-6-methoxy-2-(methylamino)-pyridine, 2,6-diamino-3,5-dimethoxy-pyridine, 3,5-diamino-2,6-dimethoxy-pyridine, 1,3-diaminobenzene, 2,4-diamino-1-(2-hydroxyethoxy)-benzene, 2,4-diamino-1-(3-hydroxypropoxy)-benzene, 2,4-diamino-1-(3-methoxypropoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[(di(s-hydroxy-ethyl)amino]- aniline, 4-amino-2-di[(2-hydroxyethyl)amino]-1-ethoxybenzene, 5-methyl-2-(1-methylethyl)-phenol, 3-[(2-hydroxyethyl)amino]-aniline, 3-[(2-aminoethyl)-amino]-aniline, 1,3-di(2,4-diaminophenoxy)-propane, di(2,4-diaminophenoxy)-methane, 1,3-diamino-2,4-dimethoxybenzene, 2,6-bis(2-hydroxyethyl)amino-toluene, 4-hydroxyindole, 3-dimethylamino-phenol, 3-diethylamino-phenol, 5-amino-2-methyl-phenol, 5-amino-4-fluoro-2-methyl-phenol, 5-amino-4-methoxy-2-methyl-phenol, 5-amino-4-ethoxy-2-methyl-phenol, 3-amino-2,4-dichloro-phenol, 3-amino-2-methyl-phenol, 3-amino-2-chloro-6-methyl-phenol, 3-amino-phenol, 2-[(3-hydroxyphenyl)-amino]-acetamide, 5-[(2-hydroxy-ethyl)amino]-2-methyl-phenol, 3-[(2-hydroxy-ethyl)amino]-phenol, 3-[(2-methoxyethyl)amino]-phenol, 5-amino-2-ethyl-phenol, 2-(4-amino-2-hydroxyphenoxy)-ethanol, 5-[(3-hydroxypropyl)amino]-2-methyl-phenol, 3-[(2,3-dihydroxypropyl)-amino]-2-methyl-phenol, 3-[(2-hydroxyethyl)-amino]-2-methyl-phenol, 2-amino-3-hydroxy-pyridine, 5-amino-4-chloro-2-methyl-phenol, 1-naphthol, 1,5-dihydroxy-naphthalene, 1,7-dihydroxy-naphthalene, 2,3-dihydroxy-naphthalene, 2,7-dihydroxy-naphthalene, 2-methyl-1-naphthol-acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 1,3-dihydroxy-2,4-dimethylbenzene, 3,4-methylenedioxy-phenol, 3,4-methylenedioxy-aniline, 5-[(2-hydroxyethyl) amino]-1,3-benzodioxol, 6-bromo-1-hydroxy-3,4-methylenedioxy-benzene, 3,4-diamino-benzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxy-indole, 5,6-dihydroxy-indoline, 4-hydroxy-indole, 5-hydroxy-indole, 6-hydroxy-indole, 7-hydroxy-indole and 2,3-indolindione, or their salts.

9. The agent of claim 6, wherein it contains additionally at least one further developer substance and/or at least one substantive dye.

10. The agent of claim 6, wherein the dye carrier composition is mixed with the oxidizing agent in a ratio by weight of 5:1 to 1:3.

11. The agent of claim 10, wherein the ready-for-use oxidation dyeing agent has a pH of 3 to 11.

12. The agent of claim 6, wherein it is a hair-dyeing agent.

* * * * *